US00PP19549P3

(12) United States Plant Patent
Hambali

(10) Patent No.: US PP19,549 P3
(45) Date of Patent: Dec. 9, 2008

(54) ***AGLAONEMA* PLANT NAMED 'TWYAG0060'**

(50) Latin Name: *Aglaonema*
Varietal Denomination: TWYAG0060

(75) Inventor: Gregori G. Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/654,762

(22) Filed: Jan. 18, 2007

(65) Prior Publication Data

US 2008/0184426 P1 Jul. 31, 2008

(51) Int. Cl.
*A01H 5/00* (2006.01)

(52) U.S. Cl. ..... Plt./376

(58) Field of Classification Search ..... Plt./376
See application file for complete search history.

*Primary Examiner*—Annette H Para
*Assistant Examiner*—S. B. McCormick-Ewoldt
(74) *Attorney, Agent, or Firm*—Jondle & Associates, P.C.

(57) ABSTRACT

A new *Aglaonema* plant particularly distinguished by having a very dense leafy, compact and upright highly branched growth habit, being intermediate in stature and very vigorous and producing axillary branches and numerous leaves is disclosed.

1 Drawing Sheet

Genus and species: *Aglaonema* hybrid.
Variety denomination: 'TWYAG0060'.

BACKGROUND OF THE NEW PLANT

The present invention comprises a new and distinct cultivar of *Aglaonema,* botanically known as *Aglaonema* hybrid, and hereinafter referred to by the cultivar name 'TWYAG0060'. The new cultivar originated from a hybridization made in W. Java, Indonesia. The cross was made in 2002 between the female parent, an unnamed individual plant of *A. rotundum* (unpatented) and the male parent, an unnamed individual plant of *A. commutatum* (unpatented).

The new cultivar was created in W. Java, Indonesia and has been asexually reproduced repeatedly by vegetative cuttings and tissue culture in Apopka, Fla. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Intermediate in stature;
2. Very dense leafy, compact and upright, highly branched growth habit;
3. Very vigorous; and
4. Produces axillary branches and numerous leaves.

DESCRIPTION OF PHOTOGRAPH

This new *Aglaonema* plant is illustrated by the accompanying photograph which shows the upper and lower surface of a mature leaf of the plant. The colors shown are as true as can be reasonably obtained by conventional photographic procedures.

DESCRIPTION OF THE NEW CULTIVAR

The following detailed description sets forth the distinctive characteristics of 'TWYAG0060'. The data which define these characteristics were collected from asexual reproductions carried out in Apopka, Fla. The plant history was taken on 16-month old plants started from a single 4-leaf rooted cutting, still in a vegetative state and grown in Apopka, Fla. Rooted cuttings were planted in 20-cm pots and grown in a greenhouse in May 2006. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family.*—Araceae.
- *Botanical.*—*Aglaonema* hybrid.
- *Common name.*—Chinese Evergreen.

Parentage:
- *Female parent.*—An unnamed individual plant of *A. rotundum* (unpatented).
- *Male parent.*—An unnamed individual plant of *A. commutatum* (unpatented).

Growth:
- *Form.*—Symmetrical, wider than tall; new leaves held upright, mature leaves arch outward.
- *Growth and branching habit.*—Very densely leafy, compact; upright highly branched growth habit (basal branching); intermediate in stature.
- *Height* (*from soil to top of leaf plane*).—28 cm to 32 cm.
- *Diameter* (*area of spread, measured from leaf tip to leaf tip across the canopy*).—50 cm to 58 cm.
- *Time to produce a finished flowering plant.*—16-months starting from a single 4-leaf rooted cutting and pinched twice.

*Root description.*—Abundant fleshy roots whiter than but closest to RHS 155C with finer lateral branches.

*Number of divisions or clumps per year.*—About 8 to 10 4-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Low temperature tolerance.*—To about 55° F. for several hours without damage.

Stems:

*Number of branches per plant.*—22.

*Length* (*from soil line to the junction of the newest two leaves*).—14 cm.

*Diameter.*—1.0 cm.

*Internode length.*—0.9 cm to 1.5 cm.

*Color.*—Immature: RHS 155A faintly tinged with RHS 165D and mottled with RHS 144C. Mature: RHS 164C. Oldest stems: RHS 147A with area of RHS 164C tinged with RHS 146B.

*Appearance* (*shape*).—Columnar, cylindrical upright.

*Aspect.*—Vertical, upright.

*Strength.*—Sturdy, strong, somewhat flexible.

*Axillary buds.*—Shape: Elliptic, flat. Length: 0.60 cm. Width: 0.30 cm. Color: RHS 158A tinged with RHS 49C.

Leaves:

*Arrangement.*—Alternate, single, arranged in a spiral along the stem.

*Quantity of leaves per stem.*—8.

*Quantity of leaflets per leaf.*—Single, simple.

*Young leaf* (*New expanded leaf*).—Color: Upper side: Base color much darker and greener than, but closest to a color between RHS 147A and RHS 146A suffused with spots and blotches of RHS 146D, and RHS 146D flushed with RHS 48A or RHS 49A; areas adjacent to the primary veins and midrib are marked with RHS 146D, RHS 48A and RHS 49A. Under side: Base color RHS N186C with a cast of RHS 147A (dark-green); suffusion of RHS 53C to RHS 53D spots; areas adjacent to the primary veins and midrib are RHS 53C to RHS 53D and RHS 185C to RHS 185D.

*Mature leaf.*—Color: Upper side: Base color much darker and greener than, but closest to a color between RHS 147A and RHS 139A suffused with spots and blotches of RHS 146C and RHS 146C flushed with RHS 53B to RHS 53C; areas adjacent to the primary veins and midrib are marked with RHS 146C flushed with RHS 53B to RHS 53C. Under side: Base color RHS N186C with a cast of RHS 147A (dark-green); suffusion of spots of RHS 53B to RHS 53C; areas adjacent to the primary veins and midrib are RHS 53B to RHS 53C and RHS 185B to RHS 185C.

*Length.*—15.3 cm to 19.5 cm.

*Width.*—Flattened: 9.0 cm to 11.5 cm. Not flattened: 6.0 cm to 9.5 cm.

*Shape.*—Elliptic to ovate.

*Apex.*—Acuminate.

*Base.*—Obtuse.

*Margin.*—Smooth, entire; mostly flat with some broad undulations.

*Texture.*—Smooth; new leaves shiny; mature leaves shiny to glossy; the leaf blade is convex between the main veins giving the leaf a textured appearance.

*Pubescence.*—None.

*Venation pattern.*—Pinnate, radiating outward from the midrib in a herringbone arrangement.

*Venation color* (*newly expanded leaf*).—Upper side: Primary veins: RHS 147D often flushed with RHS 48A, RHS 49A, RHS 53C. Midrib: RHS 48A, RHS 49A with streaks of RHS 146A to RHS 146B. Under side: Primary veins: RHS 49A. Midrib: RHS 50B to RHS 50C.

*Venation color* (*mature leaf*).—Upper side: Primary veins: RHS 146C often flushed with RHS 53B to RHS 53C. Midrib: RHS 53B to RHS 53C streaked with RHS 146A. Under side: Primary veins: RHS 49A. Midrib: RHS 50C.

*Petioles.*—Aspect: Vertical upright when newly expanded, becoming curved outward and about 45° with maturity. Length: 10.0 cm. Diameter: Distal: 0.45 cm. Proximal (petiole and petiole sheath clasps the stem proximally): Flattened: 2.6 cm. Natural diameter: 1.0 cm. Color: Distal: RHS 49A to RHS 49B (between the top of the wing and the base of the leaf). Proximal: RHS 49C to RHS 49D streaked with RHS 48A. Area adjacent to stem: RHS 49C to RHS 49D. Wing length: 6.7 cm. Wing diameter: Midpoint: 0.8 cm. Base: 1.0 cm. Depth: 0.5 cm. Wing color: Inside: RHS 49D, sides RHS 50B to RHS 50C. Outside-proximal: RHS 49C to RHS 49D streaked with RHS 48A. Outside-distal: RHS 48B base color, streaked and flushed with RHS 53B to RHS 53C. Area adjacent to stem: RHS 49D.

Fruit and seed set: None observed.

Disease and insect resistance: No special observations made.

COMPARISON WITH PARENTAL AND COMMERCIAL CULTIVARS

'TWYAG0060' differs from the female parent, an unnamed individual plant of *A. rotundum* (unpatented), by having a more compact growth habit and more branching than the female parent. Additionally, 'TWYAG0060' has elliptic to ovate leaves with pink and yellow-green blotches while the female parent has broadly ovate leaves lacking either pink or yellow-green blotches.

'TWYAG0060' differs from the male parent, an unnamed individual plant of *A. commutatum* (unpatented) by having a more compact growth habit and more branching than the male parent. Additionally, 'TWYAG0060' has very colorful leaves while the male parent has pale green leaves with lateral gray-green markings.

'TWYAG0060' differs from the commercial cultivar 'Red Gold' (unpatented), in that 'TWYAG0060' has a shorter and more compact growth habit than 'Red Gold'. In addition, 'TWYAG0060' has darker green leaves with maroon undersides, while 'Red Gold' has lighter green leaves with pale green undersides.

I claim:

1. A new and distinct cultivar of *Aglaonema* plant as shown and described herein.

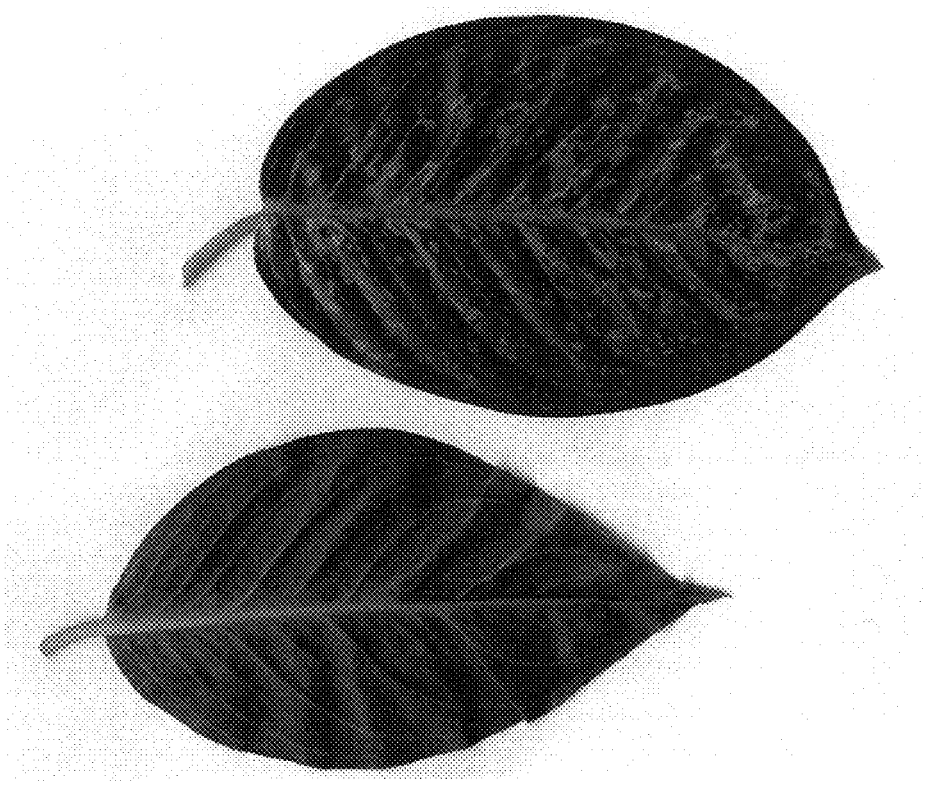

* * * * *